United States Patent
Overbeek et al.

(10) Patent No.: US 7,510,644 B2
(45) Date of Patent: Mar. 31, 2009

(54) ZEOLITES AND MOLECULAR SIEVES AND THE USE THEREOF

(75) Inventors: Rudolf Overbeek, The Woodlands, TX (US); Nelleke van der Puil, Amsterdam (NL); Chuen Y. Yeh, Edison, NJ (US); Lawrence L. Murrell, Plainfield, NJ (US); Yun-Feng Chang, Kemah, TX (US); Philip Jay Angevine, Woodbury, NJ (US); Johannes Hendrik Koegler, Heidelberg (DE)

(73) Assignee: Lummus Technology Inc., Bloomfield, NJ (US)

( * ) Notice: Subject to any disclaimer, the term of this patent is extended or adjusted under 35 U.S.C. 154(b) by 490 days.

(21) Appl. No.: 11/023,724

(22) Filed: Dec. 28, 2004

(65) Prior Publication Data

US 2005/0194289 A1   Sep. 8, 2005

Related U.S. Application Data

(63) Continuation-in-part of application No. 10/422,464, filed on Apr. 24, 2003, now Pat. No. 6,844,479, which is a continuation-in-part of application No. 09/981,926, filed on Oct. 17, 2001, now Pat. No. 6,809,055.

(60) Provisional application No. 60/242,110, filed on Oct. 20, 2000.

(51) Int. Cl.
   *C10G 11/00*  (2006.01)
   *C10G 11/04*  (2006.01)
   *C01B 39/26*  (2006.01)
   *C01B 39/42*  (2006.01)

(52) U.S. Cl. .................. 208/120.01; 208/139; 208/264; 585/467; 585/475; 585/481; 423/705

(58) Field of Classification Search ................. 208/264, 208/120.1, 139, 120.01; 585/467, 475, 481; 423/705

See application file for complete search history.

(56) References Cited

U.S. PATENT DOCUMENTS

| 3,308,069 | A | 3/1967 | Wadlinger et al. |
| 3,923,641 | A | 12/1975 | Morrison |
| 4,104,294 | A | 8/1978 | Grose et al. |
| 4,554,145 | A | 11/1985 | Rubin |
| 4,746,763 | A | 5/1988 | Kocal |
| 4,812,223 | A | 3/1989 | Hickey, Jr. et al. |
| 4,927,525 | A | 5/1990 | Chu |
| 4,994,250 | A | 2/1991 | Occelli |
| 5,116,794 | A | 5/1992 | Skeels et al. |
| 5,139,759 | A | 8/1992 | Cannan et al. |
| 5,164,169 | A | 11/1992 | Rubin |
| 5,164,170 | A | 11/1992 | Rubin |
| 5,256,392 | A | 10/1993 | Shamshoum |
| 5,258,570 | A | 11/1993 | Skeels et al. |
| 5,304,601 | A | 4/1994 | DesCourieres et al. |
| 5,427,765 | A | 6/1995 | Inoue et al. |
| 5,457,078 | A | 10/1995 | Absil et al. |
| 5,895,828 | A | 4/1999 | Yao et al. |
| 5,980,859 | A | 11/1999 | Gajda et al. |
| 6,004,527 | A | 12/1999 | Murrell et al. |
| 6,090,991 | A | 7/2000 | Butler et al. |
| 6,303,530 | B1 | 10/2001 | Schwartz et al. |

FOREIGN PATENT DOCUMENTS

EP   0 801 027   10/1997

*Primary Examiner*—Glenn Caldarola
*Assistant Examiner*—Prem C. Singh
(74) *Attorney, Agent, or Firm*—Dilworth & Barrese, LLP.

(57) ABSTRACT

A method for making a zeolite includes providing a reaction mixture containing mixed inorganic oxides and an organic templating agent, heating the reaction mixture, removing the templating agent at a temperature of no greater than 550° C. and under conditions such that the resulting zeolite is has an AAI of at least 1.2. The zeolite is preferably zeolite beta, TEA-mordenite or TEA-ZSM-12.

14 Claims, No Drawings

ZEOLITES AND MOLECULAR SIEVES AND THE USE THEREOF

CROSS-REFERENCE TO RELATED APPLICATIONS

This application claims priority based on, and is a continuation-in-part of U.S. patent application Ser. No. 10/422,464, filed Apr. 24, 2003, now U.S. Pat. No. 6,844,479 which is a continuation in part of U.S. patent application Ser. No. 09/981,926, filed Oct. 17, 2001, now issued as U.S. Pat. No. 6,809,055, which is a continuation of U.S. provisional application Ser. No. 60/242,110, filed Oct. 20, 2000, to which the present application also claims priority. The contents of all of the aforementioned applications and patent are incorporated herein by reference.

BACKGROUND

This invention relates to zeolites and molecular sieves, and more particularly to the production of zeolites and molecular sieves and the use thereof.

Zeolites and molecular sieves are generally used in a wide variety of catalytic procedures. In general, zeolites and molecular sieves may be prepared by a procedure which involves forming the structure from a reaction mixture that includes silica and alumina, and often with an organic directing agent (often referred to as a "template") such as, but not limiting to linear amines, linear diamines, and quaternary ammonium salts. As an example, such quaternary ammonium salt may be tetraethylammonium hydroxide. The organic directing agent can be removed from the resultant zeolite by a heat treatment process, often referred to as "calcination", at an elevated temperature. The acid form of the formed zeolite structure or molecular sieve is then produced by ion exchange, such as, but not limited to, ammonium exchange, followed by further calcination. In some processes, the ammonium exchange step occurs before the calcination, thereby simplifying the sequence of steps. In many cases, the (additional) heat treatment, also referred to as calcination, is executed subsequent to a forming step. In this forming or shaping step, the zeolite or molecular sieve is produced into a shape to allow use in, for example, a fixed bed catalytic operation.

In the current art, it has been recognized that the state or characteristics of the zeolite or molecular sieve may be effected by the final heat treatment step. However, it has not been recognized that, in the heat treatment to remove the organic directing agent, the performance of the zeolite or molecular sieve is affected significantly by changing the state or characteristics of the zeolite or molecular sieve materials. Applicant has surprisingly found that controlled heat treatment or calcination to remove the organic directing agent and exposure of the zeolite or molecular sieve during this treatment to average temperatures no higher than 570° C. is desired to create acid sites of a specific nature and strength. These created acid sites, as can be measured by the temperature controlled desorption of ammonia performed in accordance with Example 3 ("TPD"), are surprisingly found to significantly enhance catalytic performance in reactions, such as, but not limited to, hydrocarbon conversion technologies, and environmental abatement technologies. Applicant has found that, contrary to what has been recognized by prior art findings, that the abundance of these sites, referred to as "strong acid sites" and measured by the temperature controlled desorption of ammonia performed in accordance with Example 3 ("TPD"), is beneficial in aromatics alkylation technologies, such as, but not limited to, the ethylation of benzene to form ethylbenzene. Applicant has also found, that in addition to the appearance of such acid sites, substantial restructuring of the zeolite or molecular sieve occurs, as can be characterized using porosity measurements, such as $N_2$ physisorption and/or mercury porosimetry. According to the current understanding, Applicant believes that a combination of the above-mentioned characteristics of zeolites and molecular sieves is desirable in optimizing performance in catalytic applications, specifically in hydrocarbon conversion applications. The combination of the above-mentioned improved characteristic and enhanced catalytic performance is found to be characterized by the Acidity-Activity Index (AAI). The AAI, as used in the Specification and claims, the ratio of the total ammonia desorbed from the zeolite at a temperature above 300° C. to the total ammonia desorbed from the zeolite at a temperature below 300° C. as measured by the temperature controlled desorption performed in accordance with Example 3 ("TPD").

Contrary to Applicants' findings, U.S. Pat. No. 5,258,570 teaches that the catalytic activity of zeolite beta can be improved by activating the formed zeolite by heating at elevated temperatures of from about 600° C. to 675° C. in order to reduce so-called "strong" acid sites. In accordance with U.S. Pat. No. 5,258,570, zeolite beta produced by conventional procedures is specifically treated to reduce acid sites to thereby increase catalyst activity.

In accordance with one aspect of the present invention, there is provided a zeolite or molecular sieve that has an increased number of so called "strong acid sites", i.e., sites as measured by the temperature controlled desorption performed in accordance with Example 3 ("TPD"). More particularly, Applicant has found that by increasing the number of strong acid sites, there is provided a substantial increase in catalyst activity.

In accordance with a preferred embodiment of the present invention, the zeolites or molecular sieve has an Acidity-Activity Index (AAI) of at least 1.0, preferably at least 1.2, and more preferably at least 1.4, and most preferably at least 1.6 wherein AAI, as used in the Specification and claims, is the ratio of the total ammonia desorbed from the zeolites or molecular sieve at a temperature above 300° C. to the total ammonia desorbed from the zeolites or molecular sieve at a temperature below 300° C. as measured by the temperature controlled desorption performed in accordance with Example 3 ("TPD").

More particularly in a preferred embodiment, the zeolites or molecular sieve is one that contains silica and alumina in a silica to alumina molar ratio of 6:1 or higher or 15:1 or higher that is prepared by use of a templating or organic directing agent that includes an organic nitrogen compound. As representative but non-limiting examples of zeolites there may be mentioned: beta, TEA-mordenite, TEA-ZSM-12, MCM-22, MCM-36, MCM-39, MCM-41, MCM-48, PSH-3, ZSM-5, Breck-6, ZSM-12, ZSM-22, ZSM-23, ZSM-35, ZSM-48, SSZ-32, etc. A preferred zeolite is zeolite beta although the invention is not limited to the preferred zeolite.

In accordance with a further aspect of the present invention, Applicant has found that a zeolite or molecular sieve having an improved catalytic activity may be produced by increasing the strong acid sites thereof. In this respect, Applicant has found that during the procedures for producing zeolites and molecular sieves, and in particular the procedure for removing the organic nitrogen templating agent, the conditions employed therein should be controlled to preserve strong acid sites. In this respect, strong acid sites are maintained by employing process conditions which prevent loss of those sites that are proven to be beneficial in catalytic conversion applications and are be characterized by its AAI ratio. It is believed that those sites can be ascribed to be a specific kind of tetrahedral aluminum sites in the zeolites or molecular sieve structure.

In this respect, in removing the organic nitrogen templating agent (in general, at least 50% thereof is removed and in a preferred embodiment essentially all is removed), heating is controlled to prevent exposure to average temperatures that are above about 575° C. and preferably the heating is to an average temperature of no greater than 550° C. (in general, at least 50% thereof is removed and in a preferred embodiment essentially all is removed). Moreover, in a preferred embodiment, heating should be controlled so to in a controlled manner increase the temperature of the material to the final calcination temperature. In this respect carefully means that the temperature increase of the material is not so fast that local overheating to temperatures above about 575° C. is prevented and/or minimized.

Furthermore, in one preferred catalyst preparation step, the calcination to remove the templating agent is performed in a shallow bed in order to reduce local overheating or the occurrence of hot spots. Alternatively, a deep catalyst bed could be employed if the flowing gas is of sufficiently high superficial velocity such that the heat transfer rate maintains the catalyst bed temperature at any point to no more than about 25° C. difference from the average bed temperature. In yet another method, overheating during the calcination can be minimized by employing intermediate stops in the temperature ramp or to control hot spots by reducing/controlling oxygen flow thereby controlling heating by combustion of the organic directing agent. Other possibilities known in the art may be employed to minimize local overheating or the occurrence of hot spots.

Applicants have further found that steam may affect the catalytic activity of the zeolite or molecular sieve. As a result, in a preferred embodiment, in calcining the zeolites or molecular sieve, the zeolites or molecular sieve is slowly heated to the final calcination temperature. Controlled heating to temperatures up to 300° C., aimed at minimizing exposure to temperatures above 300° C., removes water before high temperatures are reached so as to prevent steaming, and thereby preserve strong acid sites. In one embodiment this can be effected by applying slow ramp rates, such as, for example, less than 10° C./min, preferably less than 5° C./min.

In yet another embodiment, an intermediate stop in the ramp at 300° C. can be employed to minimize exposure to significantly more elevated temperatures than 300° C.

The current working model is that the so-called "strong acid sites" are reduced primarily as a result of a loss of a specific type of tetrahedral aluminum. As a result, in accordance with an aspect of the present invention, in producing a zeolite or molecular sieve, processing conditions that reduce the amount of the specific type of tetrahedral aluminum and thereby reduce the number of strong acid sites should be minimized or avoided in order to provide for improved catalyst activity. As hereinabove indicated, in order to minimize the loss of the specific tetrahedral aluminum and thereby maintain a certain minimum amount of strong acid sites, the conditions at which the templating agent is removed should be controlled so as to reduce and/or eliminate exposure to temperatures above about 550° C. for a prolonged period of time. In addition, in a preferred embodiment steaming should be avoided; for example, but not limited to, by slow heating to the final calcination temperature.

Moreover, processing of the zeolite or molecular sieve after the removal of the templating agent should also be controlled to reduce and/or eliminate exposure to temperatures above about 550° C. For example, the exchange steps and final calcination of the ion exchanged zeolite or molecular sieve should occur at moderate temperatures. Ion exchange includes, but is not limited to, exchange of Na with $NH_4NO_3$ to produce the $NH_4$-form of the zeolite or molecular sieve. In addition, use of organic agents in procedures for extruding the zeolite or molecular sieve into a desired shape or form should also be minimized or avoided.

The prior art did not recognize that strong acid sites in zeolites and molecular sieves increase catalytic activity and that processing conditions for producing zeolite and molecular sieves should be controlled to prevent loss of strong acid sites. In the prior art, processing steps after formation of the zeolites or molecular sieve reduced the number of strong acid sites to values below those of the present invention, and such reduction resulted in a reduction in catalytic activity.

The zeolite and molecular sieves of the present invention may be combined with other materials, as known in the art. For example, zeolite and molecular sieves may optionally be metal cation exchanged following the hydrogen forming cation exchange. If the zeolite and molecular sieves are metal cation exchanged after the hydrogen forming cation exchange, the zeolite or molecular sieve component thereof preferably includes a number of acid sites as hereinabove described. As representatives of metal cations, there may be mentioned cations of group IIA, group IIIA, groups IIIB to VIIB. The use of such metal cations is known in the art and the incorporation of such additional metal cations, and the amount thereof is deemed to be within the skill of the art from the teachings herein. Similarly, the zeolite or molecular sieve may be employed with one or more inorganic oxide matrix components, which is generally combined with zeolite and molecular sieves during the exchange with a metal cation if used. Such matrix components are general inorganic oxides such as silica-aluminas, clays, aluminas, silicas, etc. The matrix may be in the form of a sol, hydrogel or gel and is generally an alumina, silica or silica-alumina component such as a conventional silica-alumina catalyst. The matrix may be catalytically active or inert. In a preferred embodiment, when combined with a matrix, the zeolite or molecular sieve component has a number of strong acid sites, as hereinabove described.

As hereinabove described, in order to maintain strong acid sites, the processing conditions should be controlled to avoid exposing the zeolite or molecular sieve to elevated temperatures for a prolonged period of time.

The zeolite and molecular sieves of the present invention may be employed for catalytically converting a feedstock wherein the zeolite or molecular sieve forms all or a portion of a catalyst in a reaction zone. A feedstock is introduced into the reaction zone for contact with the catalyst under conditions effective to convert the feedstock into a desired product.

Substantially any feedstock or combination of feedstocks may be employed in the present invention. Such feedstock, i.e., reactant component or components, may be gaseous, solid or liquid at ambient conditions, i.e., 20° C. and atmospheric pressure. The feedstock may be organic or a combination of inorganic and organic components. The present reaction system is particularly applicable to organic feedstocks, preferably having molecules comprising carbon and hydrogen, and optionally one or more other elements. This other element is preferably selected from the group consisting of oxygen, sulfur, halogen, nitrogen, phosphorus and mixtures thereof.

The product or products obtained from the feedstock/zeolite or molecular sieve catalyst contacting will, of course, depend, for example, on the feedstock, catalyst and conditions employed. As with the feedstock, the product or products can be organic or a combination of inorganic and organic components. Preferably, the desired product is organic. However, it should be noted that a necessary, and therefore desired, reaction by-product may be inorganic even when the primary product sought is organic. This is exemplified by the conversion of methanol to light olefins plus water. The organic product or products have molecules which preferably include carbon and hydrogen. The desired product or products preferably have kinetic diameters which allow such product or products to be removed from or escape from the pores of the zeolite or molecular sieve catalyst composition.

The amount of zeolite or molecular sieve catalyst in the reaction zone may vary over a wide range depending, for example, on the specific processing application involved.

In addition to the feedstock, a diluent may be used in conjunction with the feedstock if desired and/or beneficial to the overall process. Such diluent may be mixed or combined with the feedstock prior to the feedstock zeolite or molecular sieve catalyst contacting or it may be introduced into the reaction zone separately from the feedstock. Such diluent preferably acts to moderate the rate, and possibly also the extent, of feedstock chemical conversion and may also act to aid in temperature control. In certain embodiments, the diluent is preferably substantially continuously fed to the reaction zone during the process. Typical of the diluents which may be employed in the instant process are helium, argon, nitrogen, carbon monoxide, carbon dioxide, hydrogen, hydrocarbons and mixtures thereof. The amount of diluent employed, if any, may vary over a wide range depending on the particular application involved. For example, the amount of diluent may be in an amount in the range of about 0.1% or less to about 100 times or more of the moles of feedstock.

The conversion conditions at which the process occurs can vary widely depending, for example, on the specific feedstock and catalyst employed and on the specific product or products desired. The present process is particularly applicable with feedstock zeolite or molecular sieve catalyst contacting temperatures in excess of about 50° C., more preferably in excess of about 100° C., and with pressures of from about atmospheric to about 2000 psig. The residence time of the feedstock in the reaction zone may be independently selected depending, for example, on the specific feedstock and catalyst employed, and on the specific product or products desired.

Preferably the organic feedstock is a hydrocarbon feedstock, and the catalytic-conversion process is a hydrocarbon-conversion process. Substantially any hydrocarbon-conversion process which is capable of being catalyzed by a zeolite or molecular sieve catalyst composition can be conducted in accordance with this invention. Illustrative of such hydrocarbon conversion processes include, for example, cracking, hydrocracking, alkylation for both the aromatic and isoparaffin types, isomerization including normal-paraffin or xylene isomerization, polymerization, reforming, hydrogenation, dehydrogenation, transalkylation, dealkylation, hydration, dehydration, and hydrogenolysis.

Using zeolite or molecular sieve catalyst compositions which contain a hydrogenation promoter such as platinum or palladium, heavy petroleum residual stocks, cyclic stocks and other charge stocks can be hydrocracked at temperatures in the range of 200°-450° C. using molar ratios of hydrogen to hydrocarbon in the range of between 2 and 80, hydrogen partial pressures between atmospheric and 200 bar, and a liquid hourly space velocity (LHSV) of from 0.1 to 20, preferably 0.5 to 10.

The zeolite or molecular sieve catalyst compositions employed in hydrocracking are also suitable for use in reforming processes in which the hydrocarbon feedstocks contact the catalyst at temperatures of from about 350°-600° C. and hydrogen partial pressures of from 1 to 35 bar, LHSV values in the range of 0.1 to 10 and hydrogen to hydrocarbon molar ratios in the range of 1 to 20, preferably between 4 and 12.

Other isomerization reactions are carried out under conditions similar to those described above for reforming. Olefins are preferably isomerized at temperatures of 200°-500° C., while heavy paraffins, naphthenes and alkyl aromatics are isomerized at temperatures of 300°-550° C. Particularly desirable isomerization reactions contemplated herein in addition to the normal paraffin isomerization described above include the conversion of n-heptane and/or n-octane to iso-heptanes, and isooctanes, methylcyclopentane to cyclohexane, meta-xylene and/or ortho-xylene to para-xylene, 1-butene to 2-butene and/or isobutene, n-hexene to isohexene, cyclohexene to methylcyclopentene, etc. The preferred cation form is a combination of the zeolite beta with polyvalent metal compounds (such as sulfides) of metals of Group IIA, Group IIB and rare earth metals.

At somewhat higher temperatures, i.e., from about 350°-550° C., preferably 450°-500° C. and usually at somewhat lower pressures within the range of about 1 to 5 bar, the same catalyst compositions are used to hydroisomerize feedstocks containing heavier normal paraffins. Preferably, the heavy paraffin feedstock comprises normal paraffins having a carbon number range of 7-20. Contact time between the feedstock and the catalyst is generally relatively short in order to avoid undesirable side reactions such as olefin polymerization and paraffin cracking. LHSV values in the range of 0.1 to 10, preferably 0.5 to 6.0 are suitable.

The crystal structure of the activated zeolite or molecular sieve catalysts and their availability in a form totally void of alkali metal content favor their use in the conversion of alkylaromatic compounds, particularly the catalytic disproportionation of toluene, xylene, trimethyl benzenes, tetramethyl benzenes and the like. In the disproportionation process, isomerization and transalkylation can also occur. Group VIII noble metal adjuvants (e.g., platinum, palladium, iridium, ruthenium, rhodium and osmium) alone or in conjunction with Group VIB metals such as tungsten, molybdenum and chromium are preferably included in the catalyst composition in amounts of from about 3 to 15 wt. % of the overall composition. Extraneous hydrogen can, but need not, be present in the reaction zone which is maintained at a temperature of from about 200° to about 400° C., pressures in the range of 5 to 150 bar and LHSV values in the range of 0.1 to 15.

Catalytic cracking processes are preferably carried out with zeolite beta compositions using feedstocks such as gas oils, heavy naphthas, deasphalted crude oil residua, etc., with gasoline being the principal desired product. Temperature conditions of about 450° C. to about 600° C., LHSV values of 0.5 to 10 and pressure conditions of from about atmospheric to 4 bar are suitable.

The invention can be applied to naphtha hydrocracking. One example of naphtha hydrocracking via zeolite beta is described in U.S. Pat. Nos. 3,923,641 and 4,812,223, which are both incorporated by reference herein in their entirety, when $C_{5+}$ naphthas, especially $C_{7+}$ naphthas, are selectively hydrocracked into lighter products. The gaseous products have a high isobutene/n-butane ratio.

In catalytic dealkylation wherein it is desired to cleave paraffinic side chains from aromatic nuclei without substantially hydrogenating the ring structure, relatively high temperatures in the range of about 450° C. to about 600° C. are employed at moderate hydrogen pressures of about 20 to 70 bar, other conditions being similar to those described above for catalytic hydrocracking. Preferred catalysts are of the same type described above in connection with catalytic dehydrocyclization. Particularly desirable dealkylation reactions contemplated herein include the conversion of methylnaphthalene to naphthalene and toluene and/or xylenes to benzene. When employed for dealkylation of alkyl aromatics, the temperature is usually at least 175° C. and ranges up to a temperature at which substantial cracking of the feedstock or conversion products occurs, generally up to about 370° C. The temperature is preferably at least 230° C. and not greater than the critical temperature of the compound undergoing dealkylation. Pressure conditions are applied to retain at least the aromatics feed in the liquid state. For alkylation the temperature can be as low as 120° C. but is preferably at least about 175° C. In alkylation of benzene, toluene and xylene, the preferred alkylating agent is selected from olefins such as ethylene, propylene and butylene.

In catalytic hydrofining, the primary objective is to promote the selective hydrodecomposition of organic sulfur and/or nitrogen compounds in the feed, without substantially affecting hydrocarbon molecules therein. For this purpose it is preferred to employ the same general conditions described above for catalytic hydrocracking, and catalysts of the same general nature described in connection with dehydrocyclization operations. Feedstocks include gasoline fractions, kerosenes, jet fuel fractions, diesel fractions, light and heavy gas oils, deasphalted crude oil residua and the like, any of which may contain up to about 5 wt. % of sulfur and up to about 3 wt. % of nitrogen.

The hydrocarbon-conversion processes may be carried out in a batch, semi-continuous, or continuous fashion. The processes can be conducted in a single reaction zone or a number of reaction zones arranged in series or in parallel, or they may be conducted intermittently or continuously in an elongated tubular zone or a number of such zones. When multiple reaction zones are employed, it may be advantageous to employ one or more of such zeolite beta catalyst compositions in series to provide for a desired product mixture. Owing to the nature of the hydrocarbon conversion process, it may be desirous to carry out the certain processes by use of the zeolite beta catalyst compositions in a dynamic (e.g., fluidized or moving) bed system or any system of a variety of transport beds rather than in a fixed bed system. Such systems would readily provide for any regeneration (if required) of the zeolite beta catalyst compositions after a given period of time. If regeneration is required, the zeolite beta catalyst compositions can be continuously introduced as a moving bed to a regeneration zone where they can be regenerated, such as for example by removing carbonaceous materials by oxidation in an oxygen-containing atmosphere. In the preferred practice of some hydrocarbon conversion processes, the zeolite beta catalyst compositions will be subject to a regeneration step by burning off carbonaceous deposits accumulated during reactions.

In a preferred embodiment of the present invention, the zeolite or molecular sieve of the present invention is employed as a catalyst in an alkylation process such as the alkylation of benzene, for example, to produce ethylbenzene. In particular, a small increase in acid sites results in a large increase in catalyst activity.

In yet another embodiment of the present invention, the zeolite employed as a catalyst in an alkylation process such as the alkylation of benzene, for example to produce ethylbenzene, is zeolite beta.

The invention will be further described with respect to the following examples; however, the scope of the invention is not limited thereby. Unless otherwise indicate all parts and percentages are by weight.

EXAMPLE 1

Zeolite beta was made according to the patent by Murrell et al. (U.S. Pat. No. 6,004,527, 1999). Spray-dried silica (486 grams, Davison 948, 60 im average particle size) was impregnated with a mixture of 202 g $Al(NO_3)_3.9H_2O$ and 800 g distilled water, dried at 120° C. for 2 hours and calcined at 500° C. for 2 hours with a heating rate of 5° C./min. The calculated silica-alumina ratio of the material was 30.

Of the resulting silica-alumina, 162 g was impregnated with 162 g of 35 wt % TEAOH (Aldrich) and subsequently with 80 g of 3.76 wt % aqueous $NaNO_3$ solution. The liquids were added slowly while stirring in a glass beaker. The impregnated solids were transferred to a 2-liter Parr autoclave that was rotating on a motor-driven roller bed. The mixture was heated for 36 hours at 157° C. in a circulating air furnace. The autoclave was cooled to room temperature, and the solids were washed and filtered with ample amounts of water. The product was dried at 120° C. in air. X-ray diffraction showed that the product contained zeolite beta with a relative crystallinity of 113%. As a reference, a commercial zeolite beta powder was used.

Next, 20 grams of the zeolite beta product (Lab Sample 1) was calcined in air with the following program: 5° C./min to 200° C., held for 1 hour, 5° C./min to 650° C., held for 6 hours, and 5° C./min to room temperature. Another portion of 20 grams of the zeolite beta product (Lab Sample 2) was calcined in air with the following program: 5° C./min to 200° C., held for 1 hour, 1° C./min to 500° C., held for 12 hours and 10° C./min to room temperature. The calcined powders were ion exchanged in 0.1 M $NH_4NH_3$ solution for 5 days at room temperature.

Of the ion exchanged sample that was calcined at 650° C. (Lab Sample 1), 2.50 grams was mixed with 3.0 grams of Nyacol alumina sol (20 wt %) and 2.0 grams of deionized water. The paste was dried at 80° C. for 2 hours and then calcined at 550° C. for 6 hours with a heating rate of 5° C./min. The resulting product contained 80 wt % zeolite beta. The sample was ground and sieved to +20/–12 mesh size, of which 1.0 gram was loaded into the alkylation reactor. The sample had a first-order observed rate constant in the alkylation of benzene to ethylbenzene of 0.31 $cm^3/g/s$ in accordance with Example 2.

Of the dried sample that was calcined at 500° C. (Lab Sample 2), 3.225 gram was mixed with 4.06 grams of Nyacol alumina sol (20 wt %) and 3 grams of distilled water. The paste was dried at 80 for 2 hours and then calcined with the following program: 5° C./min to 200° C., held for 1 hour, 5° C./min to 500° C., hold for 6 hours. The resulting product contained 80 wt % zeolite beta. The sample was ground and sieved to +20/–12 mesh size, of which 0.76 gram was loaded into the alkylation reactor. The sample had a first order observed rate constant in the alkylation of benzene to ethylbenzene of 0.95 $cm^3/g/s$ in accordance with Example 2.

EXAMPLE 2

The following describes the alkylation procedure used to test the catalytic activity of a zeolite catalyst in accordance with the present invention (Lab Sample 2 of Example 1), a zeolite catalyst calcined by conventional techniques (Lab Sample 1 of Example 1), as well as certain commercial catalysts.

The catalytic activity of zeolite catalyst was evaluated in the model reaction of benzene alkylation with ethylene to form ethylbenzene (EB).

The test reactor is a recirculating differential fixed-bed reactor. The test conditions are 300 psig at 190° C. the recirculating rate is 200 grams/minute. The feed contains 0.35 wt ethylene dissolved in benzene with feed rate at 6.0 grams per minute.

The catalyst charge is 1.0 gram at 12 to 20 mesh particle size. The catalyst is normally hot-benzene washed for about seven hours (to remove moisture) prior to regular feed introduction by a metering pump. The test lasts for 7 to 8 hours with samples taken every 30 min. for GC analysis. The first order rate constant is calculated to represent the catalyst activity.

EXAMPLE 3

The Temperature Programmed Desorption (TPD) was carried out in the micro-reactor/mass spectrometer unit, a coupling between a quartz micro-reactor and a quadrupole mass spectrometer (Hiden Analytical HPR-20).

An amount of 40-44 mg of sample in powder form was loaded into a quartz micro-reactor.

The sample was first oxidized in a gas mixture containing 5.2% oxygen in helium flowing at 30 cc/min from 30° C. to 550° C. and held at 550° C. (TPD) for 30 minutes. After the oxidation treatment, the sample was purged in helium at 550° C. for 20 minutes before cooling down to 100° C.

Ammonia adsorption was carried out at 100° C., in a gas mixture containing 4-5% ammonia in helium, flowing at 27-30 cc/min for 30 minutes.

The ammonia treated sample was purged in helium (30 cc/min) at 100° C. for 45 minutes (enough to have the ammonia mass spec signal returning to background levels) before temperature desorption started.

Ammonia TPD was conducted at 30° C./min from 100° C. to 600° C. There are two distinct desorption maximum peaks; one <200° C. and the other >300° C. Desorption below 300° C. is classified as weak acid sites whereas desorption at >300° C. is classified as strong acid sites.

Both mass 16 and mass 17 were used for ammonia. The signal for mass 17 was used for quantifying ammonia.

Quantification of ammonia desorption was based on calibration of mass spectrometer using 4-5% ammonia.

EXAMPLE 4

TABLE 1 summarizes TPD results, AAI ratio and catalytic activity.

TABLE 1

| Catalyst | Strong | Weak | $k_{eb}$ | AAI |
| --- | --- | --- | --- | --- |
| Sample 1 from Example 1 | 0.586 | 0.886 | 0.31 | 0.66 |
| Sample 2 from Example 1 | 0/844 | 0.386 | 0.95 | 2.19 |
| Commercial beta I | 0.538 | 0.618 | 0.34 | 0.87 |
| Commercial beta II-A | 0.626 | 0.578 | 0.38 | 1.08 |
| Commercial beta II-B | 0.501 | 0.463 | 0.28 | 1.08 |
| Commercial beta II-C | 0.519 | 0.533 | 0.36 | 0.97 |

\* Total amount of ammonia desorbed at temperatures above 300° C. during TPD
\*\* Total amount of ammonia desorbed at temperatures below 300° C. during TPD

EXAMPLE 5

Al Nuclear Magnetic Resonance spectra were measured for a set of samples prepared similar to examples 1 and 2. The peaks at 55 and 0 ppm can be ascribed to tetrahedral and octahedral Al, respectively. The 55-ppm peak areas (tetrahedral Al) for the sample prepared based on prior art and the sample based on this invention are 25.3 and 48.4, respectively. Similarly, the 0-ppm peak areas (octahedral) for the sample prepared based on the prior and the sample prepared based on this invention are 41.9 and 10.1, respectively. The first order rate constant for aromatic alkylation for the former sample is 0.23 $cm^3$/g-sec and the rate constant for the latter sample is 1.71 $cm^3$/g-sec.

EXAMPLE 6

Pore size distribution measurements for the samples in Example 5 are also determined with mercury porosimetry. The sample obtained based on the prior art has wide range of pore size distribution, i.e., from 50 to 50,000 angstroms in pore diameter. The sample obtained based on this invention has very narrow pore size distribution, i.e., greater than 90% of the pores are in the range of 200 to 800 angstroms.

EXAMPLE 7

As described in Example 1 above, 3.1 grams of Davison Sylopol 948 silica gel 50 micron spheres are impregnated with a mixture of 0.63 gram Al(NO)$_3$.9H$_2$O and 11.5 grams of water to obtain a Si/Al molar ratio of 30, and dried in air at 120° C. to a constant weight. Two and one-half grams (2.5 grams) of these spheres are impregnated with 1.25 grams of an aqueous 35 weight % tetrapropylammonium hydroxide solution and 1.25 grams of an aqueous 3.68 weight % NaNO$_3$ solution, giving a molar oxide ratio of:

33.6 SiO$_2$:0.56 Al$_2$O$_3$:1 TPA$_2$O:0.22 Na$_2$O:108 H$_2$O

The mixture is placed in a 35 ml stainless steel autoclave with a 10 ml Teflon insert. After 25 hours at 158° C. the ZSM-5 crystallinity of the product is 25.1% as measured by XRD versus the reference sample. The particle shape and size of the parent amorphous framework-structure spheres are retained in the product. The template (or organic directing agent) is removed with a temperature profile shown in Example 1, Lab sample 2.

EXAMPLE 8

According to the procedure of Example 7, mordenite is prepared with a solution given a molar oxide ratio of:

5.94 SiO$_2$:0.43 Al$_2$O$_3$:0.09TEA$_2$O:1 Na$_2$O:16 H$_2$O

The mixture is placed in a 35 ml stainless steel autoclave with 10 ml Teflon insert. After 46 hours at 182° C. The mordenite crystallinity of 75% is obtained from XRD while retaining the original morphology. The template is removed with a temperature profile shown in Example 1, Lab Sample 2.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A process for treating a hydrocarbon compound, comprising:
   providing a catalyst containing a zeolite prepared by
   providing a reaction mixture containing mixed inorganic oxides and a tetraethylanimonium templating agent,
   heating the reaction mixture, and, removing a tetraethylammonium templating agent at a temperature of no greater than 550° C. and under conditions such that the resulting zeolite has an AAI of at least 1.2, wherein said zeolite is selected from the group consisting of zeolite beta, TEA-mordenite and TEA-ZSM-12; and, contacting the hydrocarbon compound with said catalyst under reaction conditions sufficient for effecting the treating of the hydrocarbon compound.

2. The process of claim 1 wherein the hydrocarbon compound is an aromatic compound and the treating process is selected from the group consisting of, hydrocracking, aromatic alkylation, isoparaffin alkylation, isomerization, polymerization, reforming, hydrogenation, dehydrogenation, transalkylation, dealkylation, dehydration, hydration and hydrogenolysis.

3. The process of claim 1 wherein the treating process is hydrogenation, the reaction conditions include a temperature of from about 200° C. to about 450° C., the molar ratio of hydrogen to hydrocarbon is from about 2 to about 80, the hydrogen partial pressure is from about atmospheric to 200 bar, and the space velocity is from about 0.1 to about 20 LHSV and the catalyst includes a hydrogenation promoter selected from platinum and palladium 4. The process of claim 1 wherein the treating process is reforming and the reaction conditions include a temperature of from about 350° C. to about 600° C., a hydrogen partial pressure of from about 1 to about 35 bar, a space velocity of from about 0.1 to 10 LHSV, and a hydrogen to hydrocarbon molar ratio of from about 1 to about 20.

5. The process of claim 1 wherein the hydrocarbon feed includes olefin(s), the treating process is olefin isomerization and the reaction conditions include a temperature of from 200° C. to about 500° C.

6. The process of claim 1 wherein the treating process includes isomerization, the hydrocarbon feed includes one or more hydrocarbon compounds selected from the group consisting of n-heptane, n-octane, methylcyclopentane, m-xylene, o-xylene, 1-butene, n-hexene or cyclohexene, and a product is produced containing one or more of isoheptane, isooctane, cyclohexane, p-xylene, 2-butene, isobutene, isohexene, or methylcyclopentene, the catalyst includes zeolite beta and compound(s) of metals of Group IIA or IIB of the Periodic Table of the Elements or rare earth metals.

7. The process of claim 1 wherein the treating process is hydroisomerization, the feed includes normal paraffins having a carbon number of from about 7 to about 20, and the reaction conditions include a temperature of from about 350° C. to about 550° C., a pressure of from about 1 to about 5 bar and a space velocity of from about 0.1 to about 10 LHSV.

8. The process of claim 1 wherein the treating process is disproportionation, the feed includes alkylaromatic compounds, the catalyst includes at least one Group VIII noble metal and the reaction conditions include a temperature of from about 200° C. to about 400° C., a pressure of from about 5 bar to about 150 bar, and a space velocity of from about 0.1 to 15 LHSV.

9. The process of claim 1 wherein the treating process is catalytic cracking, the feed includes a gas oil, heavy naphtha, or deasphalted crude oil residua, the catalyst includes zeolite beta and the reaction conditions include a temperature of from about 450° C. to about 600° C., a pressure of from about atmospheric to 4 bar, and a space velocity of from about 0.5 to about 10 LHSV.

10. The process of claim 1 wherein the treating process is hydrocracking, the feed includes normal paraffins having more than five carbon atoms, the catalyst includes activated zeolite beta and one or more metals selected from platinum, palladium and nickel, and the reaction conditions include a temperature of from about 150° C. to about 350° C., a pressure of from about atmospheric to about 150 bar, and a space velocity of from about 0.5 to about 10 LHSV.

11. The process of claim 1 wherein the treating process is catalytic dealkylation, the catalyst includes activated zeolite beta and one or more metal cation selected from iron, cobalt and nickel, and the reaction conditions include a temperature of from about 450° C. to about 600° C., a hydrogen partial pressure of from about 20 bar to about 70 bar, and a space velocity of from about 0.5 to about 10 LHSV.

12. The process of claim 1 wherein the treating process is catalytic hydrofining to convert sulfur and/or nitrogen compounds in the feed, the catalyst includes activated zeolite beta and one or more metal cations selected from iron, cobalt and nickel, and the reaction conditions include a temperature of from about 450° C. to about 600° C., a hydrogen partial pressure of from about atmospheric pressure to about 4 bar, and a space velocity of from about 0.5 to about 10 LHSV.

13. The process of claim 12 wherein the hydrocarbon feed includes gasoline fraction, kerosene, jet fuel fraction, diesel fuel, light gas oil, heavy gas oil or deasphalted crude residua.

14. The process of claim 13 wherein the hydrocarbon feed contains up to about 5 wt % sulfur and up to about 3 wt % nitrogen.

* * * * *